United States Patent [19]

Long-Hsiung

[11] Patent Number: 5,533,647
[45] Date of Patent: Jul. 9, 1996

[54] SPIKE MEANS WITH AIR PASSAGE FOR DRIP CHAMBER DEVICE

[76] Inventor: Chen Long-Hsiung, 5F, No. 91-3, Chung Cheng Rd., Sec. 1, Taipei, Taiwan

[21] Appl. No.: 547,360

[22] Filed: Oct. 24, 1995

[51] Int. Cl.⁶ .................................................... B67D 5/00
[52] U.S. Cl. ............................................. 222/83; 604/414
[58] Field of Search ....................... 222/83, 85; 604/411, 604/414

[56] References Cited

U.S. PATENT DOCUMENTS 4,857,068  8/1989  Kahn .................................. 604/405

*Primary Examiner*—Gregory L. Huson
*Attorney, Agent, or Firm*—Bacon & Thomas

[57] ABSTRACT

The spike means for drip chamber device of a drip infusion set, having a cylindrical plug rod terminating into a pointed tip for piercing the rubber stopper of the infusion bottle, the cylindrical plug rod defining an independent air passage for guiding outside air to the inside of the infusion bottle, and a solution passage with two solution inlets for guiding solution from the infusion bottle to the inside of the drip chamber for further drip infusion into the body of the patient.

1 Claim, 4 Drawing Sheets

SPIKE MEANS WITH AIR PASSAGE FOR DRIP CHAMBER DEVICE

BACKGROUND OF THE INVENTION

The present invention relates to drip infusion sets, and relates more particularly to a spike means with air passage for drip chamber device for drip infusion sets which eliminates the installation of an aeroneedle in the infusion bottle.

The drip chamber of a regular drip infusion set as shown in FIG. 1, has three solution inlets disposed in communication with one another for guiding solution out of the solution bottle. When the drip infusion set is installed, an aeroneedle must be used and pierces the rubber stopper of the infusion bottle for permitting outside air to be guided into the infusion bottle so that sufficient air pressure can be obtained inside of the infusion bottle to force solution out of the infusion bottle into the drip chamber device Because of the use of the aeroneedle, the cost of the drip infusion set is relatively increased. Furthermore, the aeroneedle must be properly disposed of after its use.

SUMMARY OF THE INVENTION

The present invention has been accomplished to provide a spike means for drip chamber of drip infusion sets which eliminates the installation of an aeroneedle by providing an independent air passage for guiding outside air into the infusion bottle during the operation of the drip infusion set. According to the preferred embodiment of the present invention, the spike means for drip chamber has a cylindrical plug rod at one end for piercing the rubber stopper of an infusion bottle for guiding out a solution from the infusion bottle to the body of a patient through a tubing and a needle, wherein the cylindrical plug rod comprises a pointed tip, an air outlet and two solution inlets on the pointed tip, an air inlet remote from the pointed tip, a sloping stop edge around the periphery between the air inlet and the air outlet for stopping at the rubber stopper of the infusion bottle for permitting the air inlet to be maintained outside the infusion bottle, an air passage connected between the air inlet and the air outlet for permitting outside air to be guided into the infusion bottle, and a solution passage for guiding the solution from the infusion bottle to the inside of the blood filter tube through the solution inlet.

DETAILED DESCRIPTION OF THE PREFERRED EMBODIMENT

Figure 1:
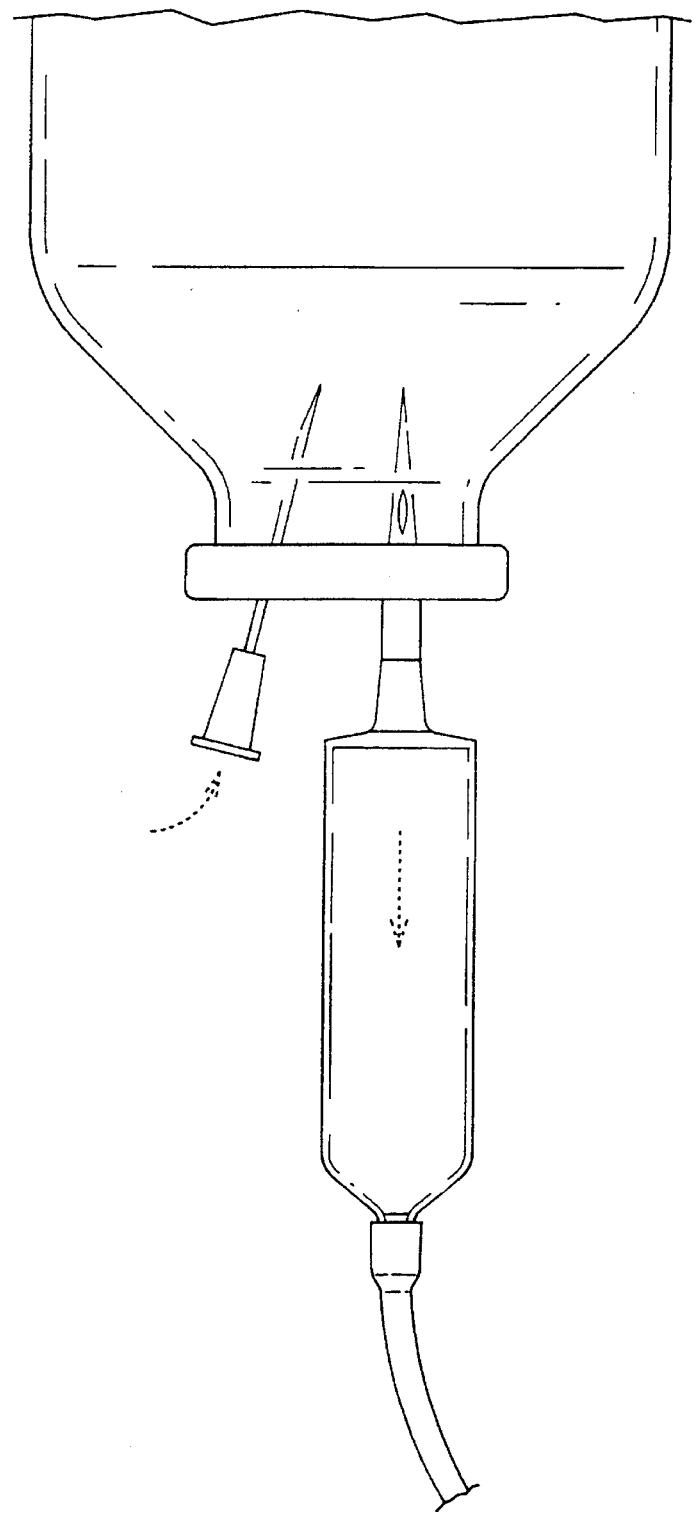
FIG. 1 shows a drip chamber and an aeroneedle installed in the infusion bottle according to the prior art.
Figure 2:
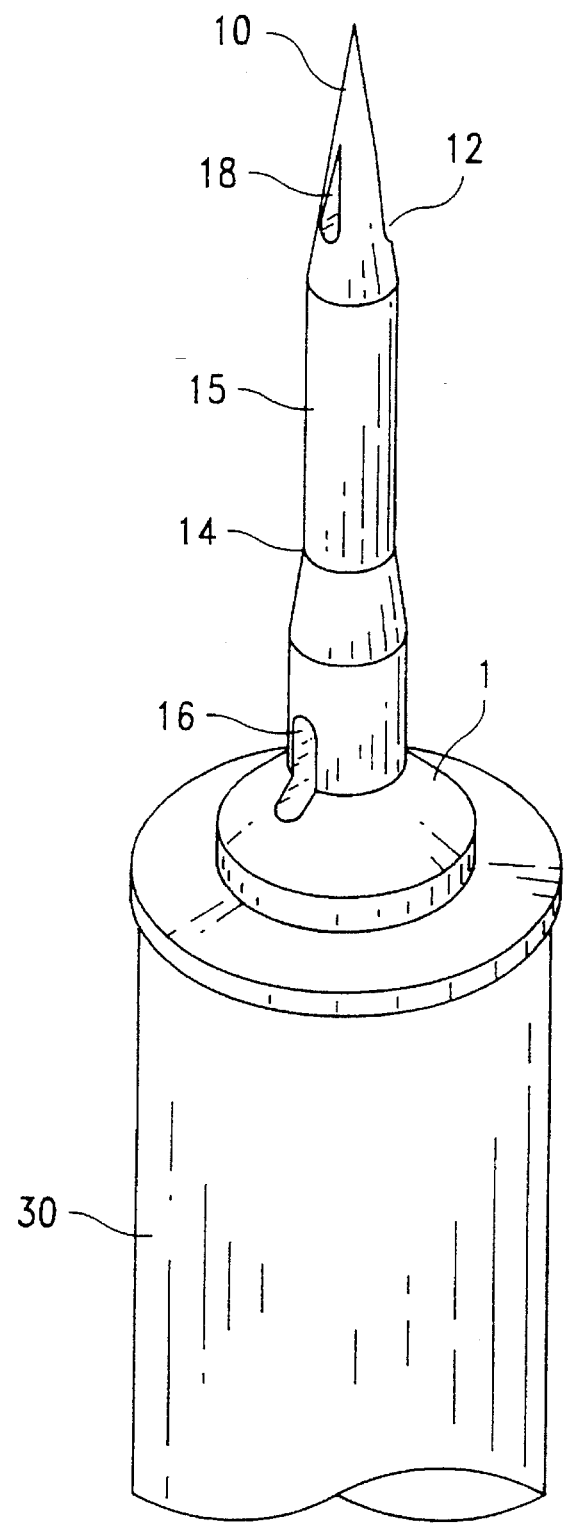
FIG. 2 is an elevational view of a spike means for drip chamber according to the present invention.
Figure 3:
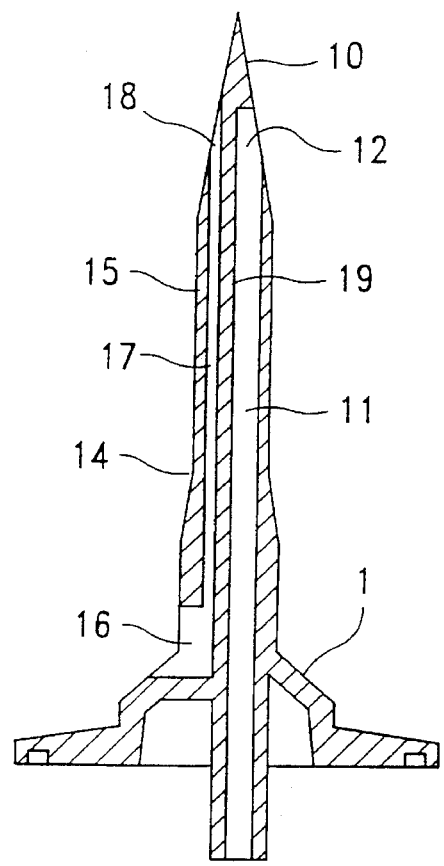
FIG. 3 is a sectional view of the spike means shown in FIG. 2.
Figure 4:
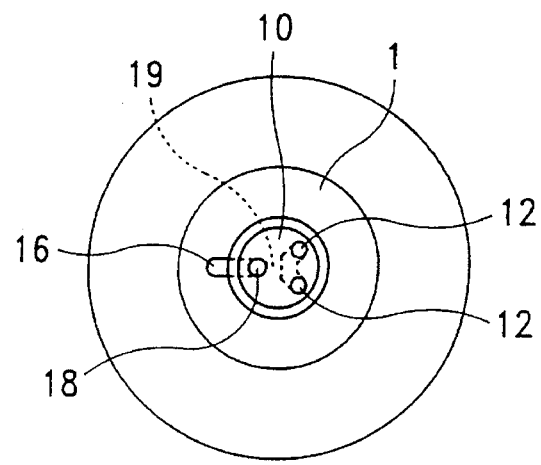
FIG. 4 is a top view of the spike means shown in FIG. 2.

Referring to FIG. 2, 3 and 4, the spike means, referenced by 1, comprises a cylindrical plug rod 15 raised front the top thereof. The cylindrical plug rod 15 comprises a pointed tip 10, an air outlet 18 and two solution inlets 12 on the pointed tip 10, an air inlet 16 adjacent to the top of the drip chamber 30 in communication with the air outlet 18, and a sloping stop edge 14 around the periphery between the air inlet 16 and the air outlet 18.

Referring to FIG. 3 again, the inside space of the cylindrical plug rod 15 of the spike means 1 is divided into an air passage 17 and a solution passage 11 by a partition board 19. The air passage 17 is connected between the air inlet 16 and the air outlet 18. The solution passage 11 is connected between the solution inlets 12 and the inside space of the drip chamber 30. Therefore, when the cylindrical plug rod 15 of the spike means 1 is inserted through the rubber stopper of the infusion bottle, air is guided from the outside to the inside of the infusion bottle through the air inlet 16, the air passage 17, and the air outlet 18, and solution is guided from the infusion bottle to the inside of the drip chamber 30 through the solution inlets 12 and the solution passage 11.

Referring to FIG. 4 again, the pointed tip 10 of the cylindrical plug rod 15 has three holes, namely, the air outlet 18, and two solution inlets 12, and the solution inlets 12 are separated from the air outlet 18 by the partition board 19.

Figure 5:
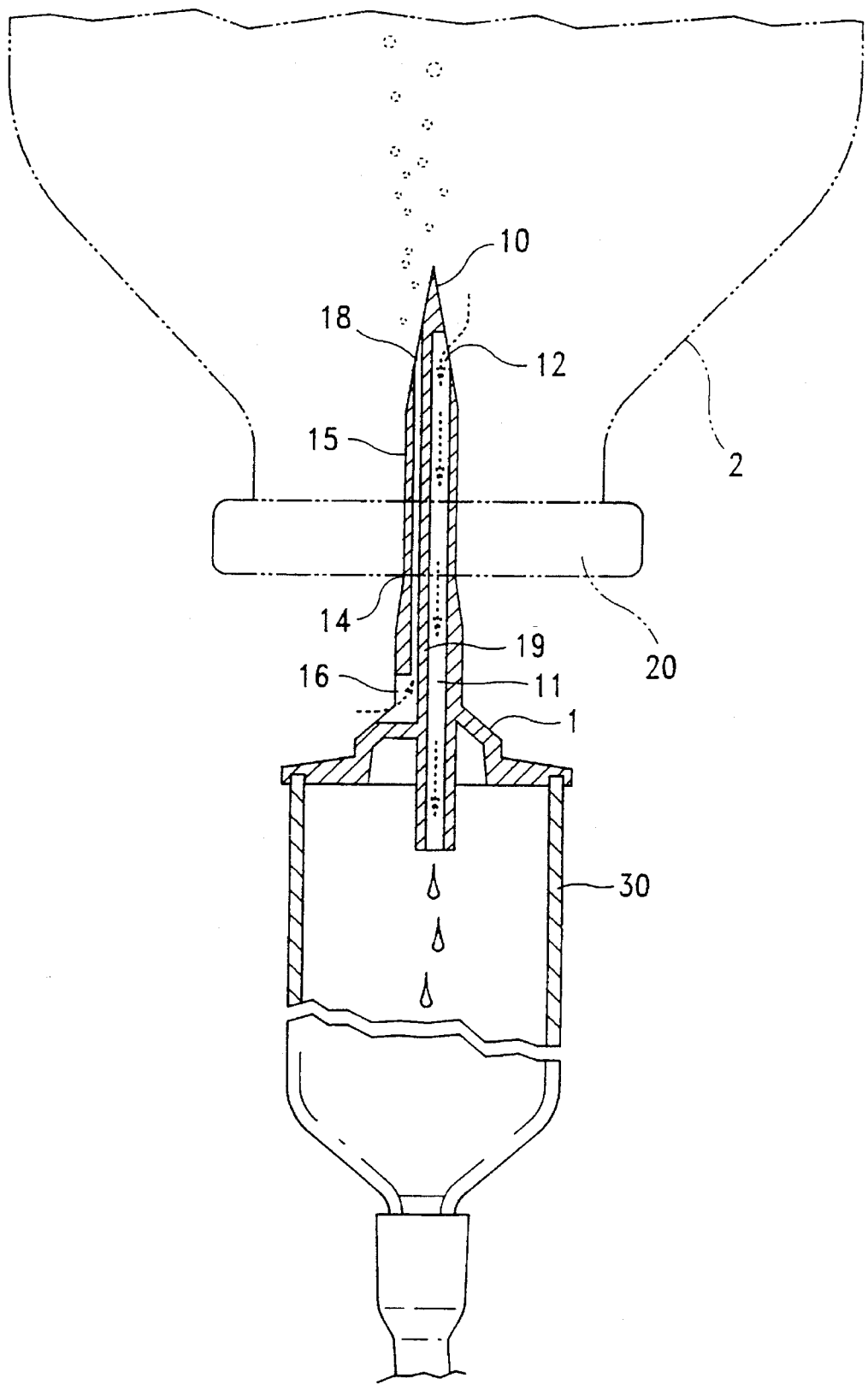
FIG. 5 is an applied view of the present invention, showing air guided into the infusion bottle and solution guided into the drip chamber.

Referring to FIG. 5, when the pointed tip 10 of the cylindrical plug rod 15 of the spike means 1 pierces the rubber stopper 20 of the infusion bottle 2 and is forced into the inside of the infusion bottle 2, the sloping stop edge 14 is stopped outside the rubber stopper 20, therefore outside air is guided into the inside of the infusion bottle 2 through the air inlet 16, the air passage 17, and the air outlet 18, and solution is guided from the infusion bottle 2 to the inside of the drip chamber 30 through the solution inlets 12 and the solution passage 11.

As indicated, the spike means for drip chamber has an independent air passage for guiding outside air into the infusion bottle. Therefore, the installation of an aeroneedle can be eliminated.

I claim:

1. A spike means for a drip chamber having a cylindrical plug rod at one end for piercing a rubber stopper of an infusion bottle for guiding out a solution from said infusion bottle to a drip chamber, wherein said cylindrical plug rod comprises a pointed tip, an air outlet and two solution inlets on said pointed tip, an air inlet remote from said pointed tip, a sloping stop edge around a periphery between said air inlet and said air outlet for stopping at said rubber stopper of said infusion bottle for permitting said air inlet to be maintained outside said infusion bottle, an air passage connected between said air inlet and said air outlet for permitting outside air to be guided into said infusion bottle, and a solution passage for guiding said solution from said infusion bottle to an inside of said drip chamber through said solution inlets.

* * * * *